United States Patent [19]

Rebuffat et al.

[11] Patent Number: 4,598,712
[45] Date of Patent: Jul. 8, 1986

[54] CIRCULAR ANASTOMOSIS

[76] Inventors: Carlo Rebuffat, Via Galilei, 17, Trento; Riccardo Rosati, Via Livorno, 4, Milano, both of Italy

[21] Appl. No.: 701,207

[22] Filed: Feb. 13, 1985

[30] Foreign Application Priority Data

Feb. 16, 1984 [IT] Italy .............................. 19652 A/84

[51] Int. Cl.$^4$ ........................................... A61B 17/04
[52] U.S. Cl. ............................ 128/334 C; 128/334 R
[58] Field of Search ............ 128/334 R, 334 C, 346, 128/303 R, 305; 285/382.4, 382.5, 260

[56] References Cited

U.S. PATENT DOCUMENTS

| | | | |
|---|---|---|---|
| 772,136 | 10/1904 | Dossert | 285/382.4 |
| 3,759,553 | 9/1973 | Carter | 285/260 |
| 3,974,835 | 8/1976 | Hardy, Jr. | 285/260 |
| 4,055,186 | 10/1977 | Leveen | 128/334 C |
| 4,469,356 | 9/1984 | Duret et al. | 285/382.5 |
| 4,470,415 | 9/1984 | Wozniak | 128/334 C |

Primary Examiner—Gene Mancene
Assistant Examiner—David I. Tarnoff

[57] ABSTRACT

A new device for the anastomosis of hollow organs to be used by means of a suitable mechanical circular anastomotic gun, is described consisting essentially in three elements fixed one inside the other, and compressing between two of them the tissue edges of the hollow dissected organs, thus enabling the natural sealing of a suture between the organs themselves.

5 Claims, 13 Drawing Figures

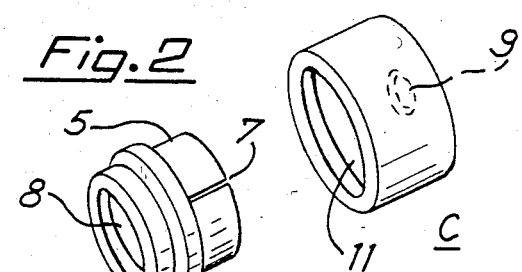
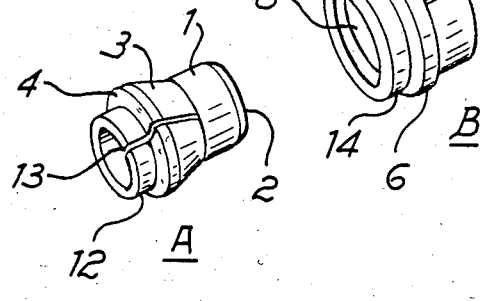
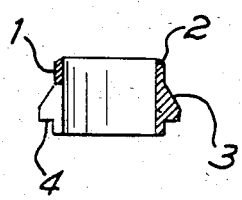
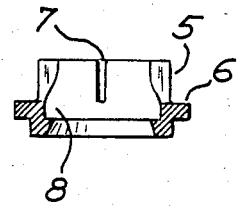
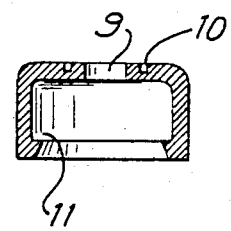
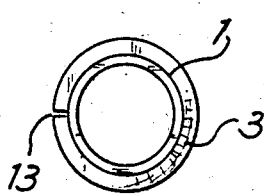
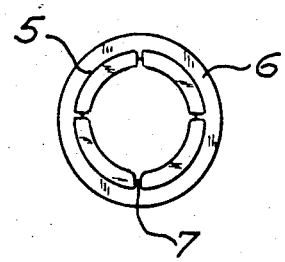
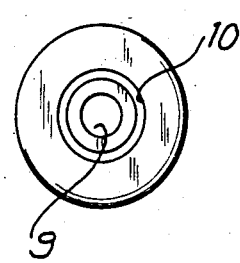

CIRCULAR ANASTOMOSIS

BACKGROUND OF THE INVENTION

The subject of the present invention is a new device for the circular anastomosis of hollow organs which makes the anastomosis compressing between two of its fixed elements the ends of the organs to be connected.

More in particular the device of the invention consists in three elements so formed to be fixed one inside the other and forming a single body with compressed between its walls the edges of the tissues of the hollow organs to be anastomosed. Protracted compression necrotizes the tissues, causing their subsequent departure together with the positioned device, after a period of time long enough so that a natural suture occurs between the mating edges of the hollow organs free ends, immediately out of the area where the compression is applied.

The techniques of mechanically performing the anastomosis of hollow organs, in the majority of the cases, utilize circular mechanical staplers, which perform the connection of the dissected hollow organs tissue edges by means of metallic staples.

It is also known a circular mechanical device the operation of which substantially differs from that of the stapling device by performing the anastomosis compressing the edges of the tissues to be connected. The compression of the tissues of organs to be joined is performed between the plane surfaces of two coaxial drilled rings, which are kept one to the other in tighten position by means of a number of metal pins and small springs coaxial with the metal pins. After a certain number of days, as the tissue compressed between the rings necrotize, the compression device separates from the hollow organ edges where the suture has by then naturally occurred and consequently it is removed in natural way.

SUMMARY OF THE INVENTION

The device of the present invention which is new both as to its whole aspect and constituting elements, even if it achieves the anastomosis of the two free ends of a dissected organ by compression as by the above mentioned known device, when compared to the same it shows undoubted advantages such as an extreme simplicity of the constituting element construction, manufacturing costs, and the possibility to have all the elements made of any suitable material such as plastic or even biodegradable material.

DETAILED DESCRIPTION OF THE INVENTION

The accompanying drawings of FIGS. 1 to 13 refer to the preferred embodiment of the invention device, but they should be not considered limiting the scope of the same. One of these preferred embodiments is represented by FIGS. 1 to 9, where:

FIG. 1 is a perspective view of the element A, which is driven by a suitable mechanical circular anastomotic gun into the element B, represented in FIG. 2, when the latter is already positioned inside the element C, represented in FIG. 3.

FIGS. 4 and 5 are a sectional view and a top view of element A respectively.

Figure 10:
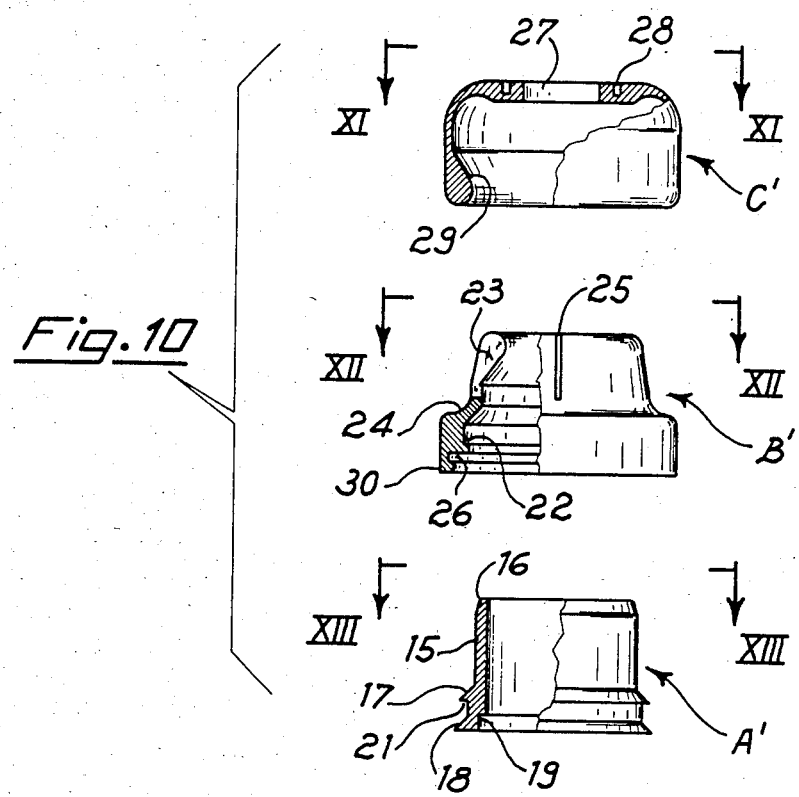

In said element A are recognized a cylindrical portion 1 having a beveled end 2, a conical portion 3 and an abutting part 4. The cylindrical portion 12, under the abutting part 4 and the abutting part 4 itself may be longitudinally crossed by a cutting 13 suitable to facilitate insertion of A into B.

FIG. 2 is a perspective view of the element B which is driven into the element C, represented in FIG. 3, by means of a suitable mechanical circular anastomotic gun.

FIGS. 6 and 7 are a sectional view and a top view of element B respectively.

In said element B is recognized a portion 5 which is externally cylindrical and internally conical because of its different thickness, thin towards the abutting part 6 and thick towards the other end. This reduced thickness of the portion 5 towards its base delimited by the abutment 6, as well as some longitudinal cuttings 7 which make the portion 5 divided in segments, makes the portion 5 itself resilient to the internal stress of the element A when inserted.

In FIGS. 6 and 7, referred to a particular embodiment of the invention, are represented four longitudinal cuttings, which make the portion 5 subdivided in four segments.

In the base internal conical portion of element B, is obtained a slot 8 for abutment with the part 4 of the element A, when the latter is urged by a suitable circular mechanical anastomotic gun.

FIG. 3 is a perspective view of the element C, which when the assembly of the device is complete, contains the elements A and B and all together form a single body.

FIGS. 8 and 9 are a sectional view and a top view of element C, respectively.

In said element C is present an axial part 9, through which the element C is pivotally connected to a suitable circular mechanical anastomotic gun; a groove 10 to facilitate separation of the device, formed by the three elements assembled together, from the circular mechanical anastomotic gun, at the moment when the latter is removed from the organism.

In the internal side of element C is obtained a slot 11 to facilitate the extension of the sements of portion S of the element B when it is subjected to the pressure of the inserted element A.

Figure 11:
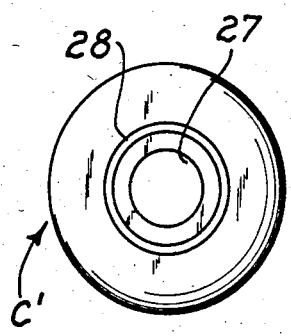
Figure 12:
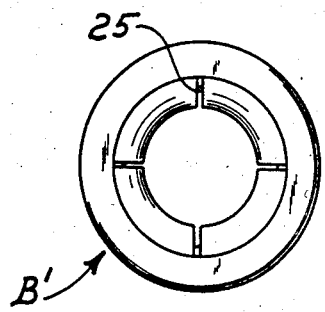
Figure 13:
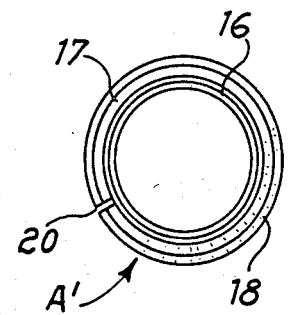

An alternative embodiment of the device of the invention is shown by the drawings in FIGS. 10–13, where FIG. 10 is a side view, partially in section along the planes XI—XI, XII—XII and XIII—XIII of elements A', B' and C' respectively constituting the device, and FIGS. 11, 12 and 13 are top view of the same elements respectively.

In the element A' are recognized a cylindrical portion 15 having a beveled end 16 and two conical portions 17 and 18 having different diameters, being bigger the one of the conical portion 18, and an abutting part 19 on which urges a movable element of a suitable circular mechanical anastomotic gun. The two conical portions 17 and 18 and partially the cylindrical portion 15 show longitudinal cutting 20 making the element A' more resilient thus facilitating its insertion into the element B'. The conical portion 17 shows an abutting part 21 that during the assembling intermediate phase of the compression device mates the abutting portion 22 of the element B'.

In said element B' is recognized a portion 23 which is externally cylindrical and internally conical because of its different thickness, thin towards the abutting part 24 and thicker towards the other end. This reduced thickness of the portion 23 towards its base delimited by the abutment 24, as well as some longitudinal cuttings 25 which make the portion 23 itself divided in segments, renders the portion 23 itself resilient to the internal stress of the element A' when inserted. In the drawing, referred to a specific embodiment of the invention, are indicated four longitudinal cuttings making the portion 23 subdivided in four segments. But these cuttings may be present also in a higher number, particularly six or eight.

In the base internal conical portion of element B', is obtained a slot 22 for abutment with the part 21 of the element A' when the latter is urged by a suitable circular mechanical anastomotic gun. In the internal lower base of the element B' is obtained a circular slot 26 and below a circular rib 30 for a proper abutting with the axial fixed element of a suitable circular mechanical anastomotic gun.

In the element C' is present an axial port 27 through which the element C' is pivotably connected to a suitable circular mechanical anastomotic gun; a groove 28 to facilitate separation of the device, formed by the three elements assembled together, from the circular mechanical anastomotic gun, at the moment when the latter is removed from the organism. The internal side 29 of the element C' is shaped for mating the outer walls of the resilient movable portions 23 of the element B' when it is subjected to the pressure of the inserted element A'.

Description of the use of a device according to the invention in practically carrying out an anastomosis of hollow organs, is given hereinafter: such description is particularly referred to the use of the device illustrated in FIG. 1-9 but it is intended to be referred also to any other possible embodiment according to the invention.

In use a suitable circular mechanical anastomotic gun carrying the device of the invention is introduced into the dissected hollow organ whose free ends proximal to the dissection area are to be anastomosed. One purse-string suture, placed on the edge of the free end of the dissected organ around the circular mechanical anastomotic gun, is tightened around the central pivot of the gun, immediately above the area where it is positioned the element B of the device according to the invention. The head portion end of the circular mechanical anastomotic gun on which the element C is supported, is then introduced into the other free end of the hollow organ proximal to the area where dissection has been performed and another purse-string suture placed on the edge of the hollow organ free end is tightened around the central pivot of the circular mechanical anastomotic gun below the element C.

The circular mechanical anastomotic gun is then operated and the elements B and C, each contained inside a free end of the dissected hollow organ by means of a purse-string suture, are drawn nearer.

The particular shape of the elements B and C makes possible that, on assembling, the tissue edges bend inwardly the elements itselves, so that when the circular mechanical anastomotic gun is closed, the two free ends of the hollow organ to be anastomosed have the bend edges mating on the upper part of B and the lower part of C, respectively.

The element A is then urged by the circular mechanical anatomotic gun and it causes the assembling of the element B into C by expanding the resilient segments 5 and following abutting of element B in the slot 11 of element C, while the element A itself gets fixed inside the element B by engagment of the abutment 4 against the slot 8.

The device consisting of the three elements A, B and C now firmly assembled each other, is then disengaged from the circular mechanical anastomotic gun by cutting along the prearranged groove 10 on the element C after the edges of the purse-string sutures have been severed.

The tissues of the so joined organs are compressed between the inner walls of the element C and the resilient segment walls of the portion 5 of the element B to which is applied a pressure from element A firmly positioned; because of this compression, the tissues necrotize and after a certain period of time they separate and are removed along with the tightened device in natural way. The period of time necessary to the tissues to necrotize and be removed is anyway longer then the time necessary to the tissue edges, which are kept in mating position on the lower part of the tighten device, the naturally heal together thus completing the anastomosis.

When it is used the device according to the embodiment illustrated in FIG. 10-13, in the end phase of the operation, the element A is urged completely inside the element B' and during this movement the conical portion 18 of the element A' forces the abutting part 22 of the element B' causing the extending of the circular rib 30 of the element B' and consequently its separation from the circular mechanical anastomotic gun support. By using said device constituted by the assembly of the element A', B' and C', it is possible to obtain, after the anastomosis has been performed, an easier separation of the suture device from the circular mechanical gun.

What we claim is:

1. Device for circular anastomosis of hollow organs, which comprises three coupling elements capable of being engaged one inside the other, the first element being placed in a first hollow organ and constituting an outer element of hollow cylindrical shape and having an upper face through which is formed an axial port, said face being provided with an annular grave spaced from said axial port, the inside surface of said first element being provided with an inwardly directed mating surface close to its lower end; the second element being placed in a second hollow organ and constituting an intermediate element of hollow cylindrical shape and provided with multiple, longitudinal slots extending through upper walls thereof and therebelow with a rim forming an abutment, the inside of said second element being provided near the lower end thereof with an annular slot and the wall thickness thereof being reduced in a region above said abutment said first and second hollow organs having their respective free ends being positioned between said inside surface of said first element and said upper walls of said second element when said second member is engaged inside of said first element; the third element also being placed in said second hollow organ and constituting a hollow inner element having a cylindrical portion and a conical portion therebelow forming an abutment for engaging the inside of said intermediate element, thereby expanding said upper walls of said second element towards said inside surface of said first element in order to compress said free ends of said first and second hollow organs together.

2. Device according to claim 1, wherein the cylindrical portion of said inner element is beveled at the upper end thereof.

3. Device according to claim 1 wherein the conical portion of said inner element and the cylindrical portion thereof are provided with a longitudinal slot to impart resiliency to the element.

4. Device according to claim 1, wherein said inner element is provided with two conical portions the diameter of the lower conical portion being larger than that of the upper conical portion.

5. Device according to claim 4, wherein said two conical portions and said cylindrical portion are provided with a longitudinal slot to impart resiliency to the element.

* * * * *